United States Patent
Cavazza

(10) Patent No.: US 7,897,641 B2
(45) Date of Patent: Mar. 1, 2011

(54) COMPOSITION FOR THE PREVENTION AND/OR TREATMENT OF THE CYTOTOXIC EFFECTS INDUCED BY THE USE OF IMMUNOSUPPRESSIVE AGENTS

(75) Inventor: Claudio Cavazza, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 161 days.

(21) Appl. No.: 10/220,185

(22) PCT Filed: Feb. 20, 2001

(86) PCT No.: PCT/IT01/00082
§ 371 (c)(1),
(2), (4) Date: Nov. 6, 2002

(87) PCT Pub. No.: WO01/64204
PCT Pub. Date: Sep. 7, 2001

(65) Prior Publication Data
US 2003/0144354 A1    Jul. 31, 2003

(30) Foreign Application Priority Data
Mar. 2, 2000  (IT) .............................. RM2000A0107

(51) Int. Cl.
*A01N 37/12* (2006.01)
*A01N 37/30* (2006.01)
*A01N 37/02* (2006.01)

(52) U.S. Cl. .................... 514/547; 514/556; 514/565

(58) Field of Classification Search .................. 514/547, 514/556, 561, 562
See application file for complete search history.

(56) References Cited

U.S. PATENT DOCUMENTS

| | | | |
|---|---|---|---|
| 4,320,145 A * | 3/1982 | Cavazza | 514/23 |
| 4,963,587 A * | 10/1990 | Iwakuma et al. | 514/562 |
| 5,270,472 A * | 12/1993 | Taglialatela et al. | 560/251 |
| 5,290,538 A * | 3/1994 | Bertermann | 514/561 |
| 5,607,691 A * | 3/1997 | Hale et al. | 424/449 |
| 5,763,408 A * | 6/1998 | Nishikawa et al. | 514/18 |
| 5,811,457 A * | 9/1998 | Corsi | 514/547 |
| 5,922,766 A * | 7/1999 | Acosta et al. | 514/561 |
| 5,955,424 A * | 9/1999 | Calvani et al. | 514/11 |
| 6,063,820 A * | 5/2000 | Cavazza | 514/739 |
| 6,245,378 B1 * | 6/2001 | Cavazza | 426/656 |
| 6,306,392 B1 * | 10/2001 | Cavazza | 424/93.51 |
| 6,348,495 B1 * | 2/2002 | Cavazza et al. | 514/547 |
| 6,552,070 B2 * | 4/2003 | Pola | 514/452 |
| 6,602,512 B1 * | 8/2003 | Cavazza | 424/400 |
| 6,641,849 B1 * | 11/2003 | Cavazza | 424/757 |
| 6,780,851 B1 * | 8/2004 | Cavazza | 514/55 |
| 6,861,554 B2 * | 3/2005 | Buononato | 562/561 |

FOREIGN PATENT DOCUMENTS

| | | |
|---|---|---|
| EP | 0 517 125 A1 | 12/1992 |
| WO | WO 9843499 A2 * | 10/1998 |
| WO | WO 00/28986 | 5/2000 |
| WO | WO 00/62773 | 10/2000 |

OTHER PUBLICATIONS

Ferrari et al., The propionyl-L-carnitine hypothesis: an alternative approach to treating heart failure, (1997), J Card Fail-3; pp. 1-2.*
Evans et al. Excretion and Metabolism of Propionyl-L-Carnitine in the Isolated Perfused Rat Kidney, vol. 281, Issue 3, 1071-1076, 1997, printed pp. 1-14 (please see p. 3 of 14, 1st line and line 11 under Materials and Methods).*
Thurman et al. (Prevention of Cyclosporine—Induced Nephrotoxicity With Dietary Glycine 1 (Transplantation, 1997, vol. 63, Issue 11, pp. 1661-1667 (Immunobiology).*

* cited by examiner

*Primary Examiner* — Sreeni Padmanabhan
*Assistant Examiner* — Timothy E Betton
(74) *Attorney, Agent, or Firm* — Lucas & Mercanti, LLP

(57) ABSTRACT

A composition is disclosed which is suitable for the prevention and/or treatment of cell and tissue abnormalities of exogenous, toxic or metabolic origin and suitable for reducing the toxic effects of cyclosporin-A and other immunosuppressive agents, which may take the form of a food supplement or of an actual medicine, containing as its active ingredients in combination or separately packaged: (a) propionyl L-carnitine or one of its pharmacologically acceptable salts, and (b) an amino acid selected from the group consisting of glycine, serine, alanine and arginine, or mixtures thereof.

18 Claims, No Drawings

COMPOSITION FOR THE PREVENTION AND/OR TREATMENT OF THE CYTOTOXIC EFFECTS INDUCED BY THE USE OF IMMUNOSUPPRESSIVE AGENTS

This application is the US national phase of international application PCT/IT01/00082 filed 20 Feb. 2001 which designated the U.S.

The present invention relates to a composition suitable for the prevention and/or treatment of cell and tissue abnormalities of exogenous, toxic or metabolic origin and suitable for reducing the toxic effects of cyclosporin A and of other immunosuppressive agents, comprising as its active ingredients, either in combination or packaged separately, propionyl L-carnitine or one of its pharmacologically salts and an amino acid selected from the group consisting of glycine, serine, alanine and arginine, or mixtures thereof.

Correspondingly, the composition may take the form and perform the functions of a food supplement or of an actual medicine, depending upon whether the composition is intended to exert a supportive or preventive action or a strictly therapeutic action according to the particular individuals for whom it is to be used.

U.S. Pat. No. 5,955,424 discloses the use of L-carnitine or of an alkanoyl L-carnitine (acetyl, propionyl, butyryl, valeryl and isovaleryl L-carnitine) and their pharmacologically acceptable salts to produce a medicine suitable for inhibiting the nephrotoxic and vasculotoxic action of cyclosporin-A and of other immunosuppressive agents such as tacrolimus, rapamycin and deoxyspergualin. The composition according to the present invention proves even more effective than the one described in the above-mentioned patent, as will be described in detail here below, owing to the potent and unexpected synergistic effect exerted by its components.

The metabolic role played by the "carnitines" (this term meaning both L-carnitine and the lower alkanoyl L-carnitines) in the process of lipid metabolism is well known, and particularly their fatty acid β-oxidation capability at the mitochondrial level and the stabilisation of the mitochondrial membranes themselves, as well as their intervention in ATP synthesis. These biochemical activities express themselves clinically in enhanced energy function at both the muscular and myocardial levels, which is particularly useful in the prevention and treatment of cardiocirculatory disorders and of various pathologies related to lipoperoxidation phenomena or to anoxic damage, especially that due to reinfusion.

From this point of view, among the other carnitines, propionyl L-carnitine has proved particularly effective not only on account of its antilipoperoxidation activity but also because of its interactions with endogenous factors such as endothelin, histamine and the prostaglandins, changes in which may be responsible for many diseases.

Glycine also exerts several different types of metabolic activity partly related to the fact that its presence is necessary for the synthesis of glutathione, but also to its ability to inhibit a number of mechanisms responsible for the cell damage induced by anoxia. It has recently been proved that glycine, like alanine and arginine, is capable of protecting the renal tubules against anoxia-induced damage and against toxic lesions induced by a number of exogenous substances with a nephrotoxic and vasculotoxic activity such as cyclosporin-A.

By means of tests conducted in a number of experimental models it has been shown that the combination of propionyl L-carnitine and an amino acid selected from the group consisting of glycine, alanine, serine and arginine, or mixtures thereof exerts an unexpected and surprising synergistic effect in the prevention and treatment of lesions of a number of important organs such as the kidney and liver induced by exogenous toxic substances such as, for example, cyclosporin A, tacrolimus, rapamycin and deoxyspergualin or by hepatotoxic substances such as carbon tetrachloride. The combination exerts a similar potent effect in states of distress such as those occurring during tissue anoxia.

An object of the present invention is therefore a composition containing as its active ingredients, either in combination or packaged separately:

(a) propionyl L-carnitine or one of its pharmaceutically acceptable salts, and
(b) an amino acid selected from the group consisting of glycine, serine, alanine and arginine, or mixtures thereof, which is particularly useful, thanks to the unexpected and potent synergistic effect exerted by its components, in the prevention and/or treatment of cell and tissue abnormalities of exogenous toxic or metabolic origin and suitable for reducing the toxic effects of cyclosporin-A and of other immunosuppressive agents such as tacrolimus, rapamycin and deoxyspergualin.

As component (b), glycine is particularly preferred.

It has also been found, advantageously, that component (a) may additionally contain a "carnitine" selected from the group consisting of L-carnitine, acetyl L-carnitine, valeryl L-carnitine, isovaleryl L-carnitine and butyryl L-carnitine or their pharmacologically acceptable salts or mixtures thereof.

In the composition according to the present invention, the weight-to-weight ratio of (a) to (b) may range from 10:1 to 1:10, and preferably from 5:1 to 1:5.

The composition according to the present invention may additionally comprise vitamins, coenzymes, mineral substances, amino acids and/or antioxidants.

The composition can be administered orally, in the form of a food supplement, or can be administered parenterally, rectally, sublingually or transdermally in the form of a medicine for the treatment of frank pathological conditions. It can therefore be packaged in solid, semisolid or liquid form, in the form, for example, of tablets, pills, capsules, granules, syrups, ampoules or drops.

The surprising synergistic effect which is produced by the combination of propionyl L-carnitine and the above-mentioned amino acids has been demonstrated by several pharmacological tests (some of which are described here below) selected in such a way as to be strongly predictive for the practical use of this composition both in the preventive/nutritional field and in the strictly therapeutic field.

Toxicology Tests

In these tests a group of Sprague Dawley rats received intraperitoneal administrations of either propionyl L-carnitine alone (0.5 g/kg) or glycine alone (0.5 g/kg) or the two compounds in combination, or oral administrations of propionyl L-carnitine alone (1 g/kg) or glycine alone (1 g/kg) or the two compounds in combination at the same doses, without any mortality being observed in the animals thus treated or any other sign of toxic effects. Prolonged oral administration of 500 mg/kg of propionyl L-carnitine or 500 mg/kg of glycine for 20 days consecutively or the two compounds in combination at the same doses also proved to be well tolerated. Neither the examination of weight gain nor the blood-chemistry tests performed at the end of treatment revealed any abnormalities of a toxic nature and the results were comparable to those observed in a well-matched group of control animals.

Tests of Cyclosporin—A Toxicity in Isolated and Perfused Rat Kidney

As is known, one of the main signs of toxicity that develops with the use of cyclosporin-A is detected at the renal level and can be evaluated functionally, cytologically and morphometrically.

Using the isolated rat kidney according to the technique described by Maack (Maack P., *Kidney Int.*, 30:142, 1986) and Shure (Shure K. H., *Delugers Arch.*, 35:4, 1975) and perfusing it with a solution containing cyclosporin-A, it is possible to detect the toxic reactions this substance induces at the renal level relating both to the renal cytomorphology, particularly at the tubular level, and to arteriolar and alveolar capillary vasoconstriction and the release of enzymes such as alanine aminopeptidase (AAP) and N-acetylglucosaminidase (NAG), the release of which is regarded as a sign of cell damage, as is the release of vasoactive substances such as histamine and endothelin-1.

Among the various "carnitines", propionyl L-carnitine has proved to be the most effective in protecting the kidney against the toxic lesions induced by cyclosporin-A.

Propionyl L-carnitine, in fact, unlike L-carnitine and acetyl L-carnitine, has proved capable not only of protecting the renal structures against lesions induced by cyclosporin-A or by tacrolimus, but also of reducing the biochemical lesions related to the cytotoxicity of these substances, such as the intracellular increase in calcium and the reduction in ATP.

A number of amino acids such as alanine and arginine have also demonstrated cytoprotective activity against the toxicity induced by cyclosporin-A at the level of functional biochemical abnormalities such as the intracellular increase in calcium or protection against lipoperoxidation phenomena, whereas they would not appear to be effective against the reduction in intracellular ATP, or against the morphological structural lesions at the glomerular level, or against the increase in toxic endothelial factors such as histamine and endothelin-1.

In the tests performed with the combination of propionyl L-carnitine and glycine, a protective effect was observed against the renal damage induced by cyclosporin-A or by tacrolimus and this effect was surprisingly greater than that which would have been expected from simple addition of their effects: this indicates a synergistic action which is responsible for an unexpectedly high protective efficacy.

In these tests a group of rats were used whose kidneys were isolated, after bilateral nephrectomy, and perfused according to the technique described by Schure and Maack.

The kidneys thus isolated were perfused by means of a pulsating pump both with a solution containing cyclosporin A or tacrolimus and with a solution containing propionyl L-carnitine or glycine or the two components in combination.

The parameters observed on the kidneys thus perfused were the capillary diameters (CD) and the Bowman's capsule diameters (BD) and equally the external and internal diameter (ID) and also the diameter at the level of the basal membrane (ED) of at least 20 proximal tubules.

A calorimetric method was used to measure both AAP and NAG on the renal venous flow. Histamine and endothelin-1 were measured with a colorimetric method or with RIA.

Lipid peroxidation was measured on samples of renal cortex as described by Longoni (Longoni B., *Int. J. Tissue React.*, 21.7.1997-Lowry O. H., *J. Biol. Bioch.*, 193:265, 1951) and ATP concentrations were determined according to the method described by Sumpio (Sumpio B. E., *Am. J. Physiol.*, 247, PT2, 1047, 1984).

Arterial pressure on the perfused kidney was measured by means of a manometer connected up to the renal artery.

The results of these tests, presented in Tables 1, 2 and 3, indicate that propionyl L-carnitine is effective in protecting the kidney both against the morphological damage and against the cellular biochemical damage induced by cyclosporin-A or by tacrolimus.

Glycine is much less effective in its protective action against lesions induced by cyclosporin-A.

Its action on the morphological damage induced by cyclosporin A and on the reduction in intracellular ATP is not significantly detectable, nor is its action on the release of vasoactive substances such as histamine and endothelin, whereas it does have a detectable protective effect on the lipid peroxidation activity induced by cyclosporin-A.

The combination of propionyl L-carnitine and glycine, on the other hand, shows an unexpected and surprising synergistic effect which manages to counteract almost entirely the vascular and cellular biochemical damage induced by cyclosporin-A or tacrolimus. The enhancement of the protective effects exerted by the combination of propionyl L-carnitine and glycine thus confirms the validity and originality of the composition which is one of the objects of the present invention and the enhancement of the protective effects that can be obtained with their combined use is associated with very promising practical therapeutic prospects.

Protective Activity Against Liver Toxicity

The cytoprotective activity exerted by propionyl L-carnitine and by a number of amino acids, including glycine, is not observable only at the renal level, but can also be seen in other organs such as the liver.

In these tests, it was observed, in fact, that the toxic damage induced in the liver by exogenous toxic substances such as, for example, carbon tetrachloride can be reduced by the prior administration of propionyl L-carnitine or glycine.

However, virtually complete inhibition of this damage can be achieved with a combination of propionyl L-carnitine and glycine. Their use in combination, in fact, also shows an unexpected and surprising synergistic activity at the hepatic level, which could not be predicted on the basis of the simple addition of their effects.

In these tests, male Sprague Dawley rats were used, which were intraperitoneally administered propionyl L-carnitine, glycine or the two compounds in combination, half an hour prior to receiving $CCl_4$. $CCl_4$ was administered at the dose of 1 mL/kg of a 20% solution in olive oil according to the technique described by Bernacchi (Bernacchi A. G., *Brit. J. Exp. Pathol.*, 61:505, 1980).

Twenty-four hours after administration of $CCl_4$, alanine aminotransferase was assayed as an indicator of enzymatic liver damage in blood from the animals thus treated, according to the colorimetric method described by Reitman (Reitman S., *Am. J. Clin. Pathol.*, 28:56, 1997), whereas from the livers taken from the same animals triglycerides were extracted with methanol and chloroform and assayed according to the method described by Kleir (Kleir, *J. Biochem. Clin. Bohenescov.*, 9:243, 1999). The livers were then fixed with Carnon fixative and, after embedding in paraplast, were stained with haematoxylin and eosin.

The surprisingly favourable results of these tests in terms of the synergistic action of propionyl L-carnitine and glycine were also confirmed by microscopic examination of liver sections. Unlike the samples from animals treated with $CCl_4$ or with $CCl_4$ and propionyl L-carnitine or glycine, those treated with the combination according to the present invention showed preservation of the cellular morphology with no nuclear or liver cell abnormality.

TABLE 1

Protective effect on renal hypertension induced by cyclosporin-A (2 mg/L) or by tacrolimus (400 µg/L) in perfused rat kidneys treated with propionyl L-carnitine (5 mg/L) or glycine (5 mg/L) or with the two compounds in combination

| | % inhibition of hypertensive effect after | |
|---|---|---|
| | 5 min | 20 min |
| Cyclosporin A | | |
| Propionyl L-carnitine | 18.2 ± 1.5 | 28.4 ± 2.1 |
| Glycine | 6.3 ± 0.9 | 6.8 ± 0.3 |
| Propionyl L-carnitine + glycine | 35.5 ± 3.1 | 48.2 ± 4.1 |
| Tacrolimus | | |
| Propionyl L-carnitine | 22.5 ± 2.3 | 30.7 ± 2.9 |
| Glycine | 4.8 ± 7.1 | 7.4 ± 0.9 |
| Propionyl L-carnitine + glycine | 36.8 ± 2.9 | 51.7 ± 6.6 |

TABLE 2

Protective effect on histamine and endothelin-1 release induced by cyclosporin-A (2 mg/L) or by tacrolimus (400 µg/L) in isolated, perfused rat kidneys treated with propionyl L-carnitine (5 mg/L) or glycine (5 mg/L) or with the two compounds in combination

| | % inhibition of release (+) | |
|---|---|---|
| | histamine | endothelin-1 |
| Cyclosporin-A | | |
| Propionyl L-carnitine | 39.5 ± 4.1 | 41.2 ± 3.8 |
| Glycine | 10.4 ± 1.1 | 8.8 ± 0.9 |
| Propionyl L-carnitine + glycine | 70.5 ± 5.5 | 65.8 ± 4.1 |
| Tacrolimus | | |
| Propionyl L-carnitine | 41.5 ± 3.9 | 34.7 ± 2.7 |
| Glycine | 7.5 ± 0.8 | 6.5 ± 0.7 |
| Propionyl L-carnitine + glycine | 67.9 ± 5.1 | 74.6 ± 6.6 |

(+) values after 1 min perfusion

TABLE 3

Protective effect on renal tubular damage induced by cyclosporin-A (2 mg/L) or by tacrolimus (400 µg/L) in isolated, perfused rat kidneys treated with propionyl L-carnitine (5 mg/L) or glycine (5 mg/L) or with the two compounds in combination and evaluated by assay of the enzymes alanine aminopeptidase (AAP) and N-acetylglucosaminidase (NAG)

| | % inhibition of release (+) | |
|---|---|---|
| | AAP | NAG |
| Cyclosporin-A | | |
| Propionyl L-carnitine | 32.8 ± 3.1 | 30.5 ± 2.6 |
| Glycine | 14.2 ± 0.9 | 16.5 ± 0.6 |
| Propionyl L-carnitine + glycine | 71.8 ± 4.6 | 68.5 ± 4.1 |
| Tacrolimus | | |
| Propionyl L-carnitine | 35.1 ± 2.9 | 30.8 ± 2.5 |
| Glycine | 18.5 ± 1.1 | 17.2 ± 0.9 |
| Propionyl L-carnitine + glycine | 81.6 ± 5.1 | 76.2 ± 6.7 |

(+) values after 5 min perfusion

TABLE 4

Protective effect of propionyl L-carnitine and glycine on glomerular morphometric abnormalities induced by cyclosporin-A

| | Morphometric indices | |
|---|---|---|
| | glomerular CD/BD | tubular ID/ED |
| Control | 0.93 ± 0.09 | 0.36 ± 0.03 |
| Cyclosporin-A (2 mg/L) | 0.78 ± 0.02 | 0.75 ± 0.08 |
| Propionyl L-carnitine (5 mg/L) | 0.86 ± 0.7 | 0.40 ± 0.06 |
| Glycine (5 mg/L) | 0.80 ± 0.5 | 0.66 ± 0.5 |
| Propionyl L-carnitine (5 mg/L) + glycine (5 mg/L) | 0.91 ± 0.7 | 0.38 ± 0.02 |

TABLE 5

Protective effect of propionyl L-carnitine and glycine and their combination on the reduction of renal ATP induced by cyclosporin-A

| | ATP (nM/g tissue) |
|---|---|
| Control | 6.70 ± 0.51 |
| Cyclosporin-A | 4.51 ± 0.41 |
| Propionyl L-carnitine | 6.05 ± 0.61 |
| Glycine | 4.56 ± 0.49 |
| Propionyl L-carnitine + glycine | 6.65 ± 0.60 |

TABLE 6

Protective effect of propionyl L-carnitine and glycine and their combination on renal lipoperoxidation induced by cyclosporin-A and evaluated by assay of the lipoperoxidation products malonaldehyde (MDA) and 4-hydroxyalkenal (4-HDA).

| | MDH + 4-HDA (nmol/mg protein) |
|---|---|
| Control | 2.1 ± 0.91 |
| Cyclosporin-A | 6.5 ± 0.52 |
| Propionyl L-carnitine | 4.2 ± 0.39 |
| Glycine | 4.8 ± 0.41 |
| Propionyl L-carnitine + glycine | 2.9 ± 0.19 |

TABLE 7

Protection against liver damage in rats intoxicated with $CCL_4$

| | Alanine aminotranferase activity (ALT U/L) | Triglycerides (mg/g) |
|---|---|---|
| Controls | 12.5 ± 1.7 | 6.5 ± 0.7 |
| $CCl_4$ | 105.4 ± 3.8 | 26.5 ± 0.11 |
| Propionyl L-carnitine (300 mg/kg) | 75.8 ± 5.5 | 18.8 ± 1.8 |
| Glycine (300 mg/kg) | 90.2 ± 8.6 | 22.2 ± 2.1 |
| Propionyl L-carnitine (300 mg/kg) + glycine (300 mg/kg) | 22.4 ± 1.9 | 8.5 ± 0.9 |

Provided here below by way of illustration are a number of non-limiting examples of compositions according to the present invention:

| Tablets or capsules | |
|---|---|
| 1) Propionyl L-carnitine | 1 g |
| Glycine | 1 g |
| 2) Propionyl L-carnitine | 0.5 g |
| Acetyl L-carnitine | 0.5 g |
| L-carnitine | 0.5 g |
| Isovaleryl L-carnitine | 0.5 g |
| Glycine | 1 g |
| 3) Propionyl L-carnitine | 1 g |
| Glycine | 0.5 g |
| Arginine | 0.5 g |
| Alanine | 0.5 g |
| Granule sachets | |
| 4) Propionyl L-carnitine | 2 g |
| Glycine | 2 g |
| 5) Propionyl L-carnitine | 1 g |
| Glycine | 2 g |
| Arginine | 2 g |
| Alanine | 2 g |
| Single-dose vials | |
| 6) Propionyl L-carnitine | 2 g |
| Glycine | 2 g |
| 7) Propionyl L-carnitine | 1 g |
| Acetyl L-carnitine | 1 g |
| L-carnitine | 1 g |
| Isovaleryl L-carnitine | 1 g |
| Glycine | 1 g |
| 8) Propionyl L-carnitine | 1 g |
| Glycine | 1 g |
| Arginine | 1 g |
| Alanine | 1 g |
| Injectable ampoules | |
| 9) Propionyl L-carnitine | 0.5 g |
| Glycine | 0.5 g |
| 10) Propionyl L-carnitine | 0.5 g |
| Glycine | 0.5 g |
| Arginine | 0.5 g |
| Alanine | 0.5 g |
| 11) Propionyl L-carnitine | 0.5 g |
| Acetyl L-carnitine | 0.5 g |
| L-carnitine | 0.5 g |
| Isovaleryl L-carnitine | 0.5 g |
| Glycine | 0.5 g |
| Arginine | 0.5 g |
| Alanine | 0.5 g |
| Single-dose vials or granules | |
| 12) Propionyl L-carnitine | 1 g |
| Acetyl L-carnitine | 0.5 g |
| Isovaleryl L-carnitine | 0.5 g |
| Glycine | 0.5 g |
| Arginine | 0.5 g |
| Alanine | 0.5 g |
| Serine | 0.5 g |
| Glutamine | 0.5 g |
| 13) Propionyl L-carnitine | 1 g |
| Glycine | 0.5 g |
| Arginine | 0.5 g |
| Alanine | 0.5 g |
| Serine | 0.25 g |
| Eicosapentaenoic acid (EPA) | 0.350 g |
| Docosapentaenoic acid (DHA) | 0.150 g |
| 14) Propionyl L-carnitine | 1 g |
| Glycine | 0.5 g |
| Arginine | 0.5 g |
| Alanine | 0.5 g |
| Serine | 0.25 g |
| Acetylcysteine | 0.100 g |

What is meant by a pharmacologically acceptable salt of L-carnitine or of an alkanoyl L-carnitine is any salt of these with an acid which does not give rise to unwanted toxic or side effects. These acids are well known to pharmacologists and to experts in pharmaceutical technology.

Non-limiting examples of such salts are the following: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate, acid oxalate; sulphate, acid sulphate; trichloroacetate; trifluoroacetate and methane sulphonate.

A list of FDA-approved pharmacologically acceptable acids is given in *Int. J. Pharm.*, 33, 1986, 201-217, the latter publication being incorporated in the present specification by reference.

The invention claimed is:

1. A combination composition consisting of:
   (a) propionyl L-carnitine or a pharmacologically acceptable salt thereof; and
   (b) an amino acid selected from the group consisting of glycine, alanine, arginine and serine or the pharmacologically acceptable salts thereof or mixtures thereof
wherein the weight ratio (a):(b) ranges from 10:1 to 1:10.

2. A combination composition consisting of:
   (a) propionyl L-carnitine or a pharmacologically acceptable salt thereof and a carnitine selected from the group consisting of L-carnitine, valeryl L-carnitine, isovaleryl L-carnitine and butyryl L-carnitine or their pharmacologically acceptable salts or mixtures thereof; and
   (b) an amino acid selected from the group consisting of glycine, alanine, arginine and serine or the pharmacologically acceptable salts thereof or mixtures thereof
wherein the weight ratio (a):(b) ranges from 10:1 to 1:10.

3. The composition of claim 1, wherein the weight ratio (a):(b) ranges from 5:1 to 1:5.

4. The composition of claim 1 wherein the pharmacologically acceptable salt is selected from the group consisting of: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate; acid oxalate; sulphate, acid sulphate; trichloroacetate; trifluoroacetate and methane suiphonate.

5. The composition of claim 1, orally administrable, in the form of a dietary supplement.

6. The composition of claim 1, orally, parenterally, rectally, sublingually or transdermally administrable, in the form of a medicament.

7. A method for treating cellular and tissue alterations due to the toxic effects of immunosuppressants which comprises administering to a subject in need thereof a combination composition of claim 1.

8. The method of claim 7 wherein the immunosuppressants are selected from the group consisting of cyclosporin-A and tacrolimus.

9. The composition of claim 1 as a dietary supplement in solid, semisolid or liquid form.

10. The composition of claim 1, in solid, semi-solid or liquid form.

11. The dietary supplement of claim 9, in the form of tablets, lozenges, pills, capsules, granulates or syrups.

12. The composition of claim 10, in the form of tablets, lozenges, pills, capsules, granulates, syrups, vials or drops.

13. A method for the treatment of nephrotoxic, vasculotoxic or cytotoxic lesions brought about by the use of immunosuppressants selected from the group consisting of cyclosporin-A and tacrolimus, which comprises administering to a subject in need thereof a combination composition of claim 1.

14. A method for treating cellular and tissue alterations of exogenous, toxic or metabolic origin and decreasing the toxic effects of immunosuppressants which comprises administering to a subject in need thereof a combination composition of claim 1.

15. A method for the treatment of nephrotoxic, vasculotoxic or cytotoxic lesions brought about by the use of immunosuppressants selected from the group consisting of cyclosporin-A and tacrolimus, which comprises administering to a subject in need thereof a combination composition of claim 1,
wherein the weight ratio of (a):(b) is 1:1.

16. A method for treating cellular and tissue alterations of exogenous, toxic or metabolic origin and decreasing the toxic effects of immunosuppressants which comprises administering to a subject in need thereof a combination composition of claim 1,
wherein the weight ratio of (a):(b) is 1:1.

17. A combination composition consisting of:
(a) propionyl L-carnitine or a pharmacologically acceptable salt thereof; and
(b) an amino acid selected from the group consisting of glycine, alanine, arginine and serine or the pharmacologically acceptable salts thereof or mixtures thereof; and
(c) vitamins, coenzymes, mineral substances, aminoacids or antioxidants
wherein the weight ratio (a):(b) ranges from 10:1 to 1:10.

18. A method for the treatment of nephrotoxic lesions brought about by the use of immunosuppressants selected from the group consisting of cyclosporin-A and tacrolimus, which comprises administering to a subject in need thereof a combination composition of claim 1.

* * * * *